(12) United States Patent
O'Brien et al.

(10) Patent No.: US 9,307,913 B2
(45) Date of Patent: Apr. 12, 2016

(54) PATIENT MONITORING

(75) Inventors: Terence Kevin O'Brien, London (GB); Eric Stephen Mills, London (GB)

(73) Assignee: LIDCO GROUP PLC, London (GB)

( * ) Notice: Subject to any disclaimer, the term of this patent is extended or adjusted under 35 U.S.C. 154(b) by 846 days.

(21) Appl. No.: 12/248,918

(22) Filed: Oct. 10, 2008

(65) Prior Publication Data

US 2009/0131805 A1 May 21, 2009

Related U.S. Application Data

(63) Continuation-in-part of application No. 12/099,411, filed on Apr. 8, 2008, now abandoned.

(60) Provisional application No. 60/960,720, filed on Oct. 11, 2007.

(30) Foreign Application Priority Data

Oct. 11, 2007  (EP) .................................. 07254032

(51) Int. Cl.
| | |
|---|---|
| *A61B 5/02* | (2006.01) |
| *A61B 5/0205* | (2006.01) |
| *G06F 19/00* | (2011.01) |
| *A61B 5/00* | (2006.01) |

(Continued)

(52) U.S. Cl.
CPC ............ *A61B 5/0205* (2013.01); *A61B 5/02028* (2013.01); *A61B 5/743* (2013.01); *G06F 19/3406* (2013.01); *A61B 5/022* (2013.01); *A61B 5/024* (2013.01); *A61B 5/029* (2013.01); *A61B 5/0215* (2013.01); *A61B 5/0402* (2013.01); *A61B 5/145* (2013.01)

(58) Field of Classification Search
None
See application file for complete search history.

(56) References Cited

U.S. PATENT DOCUMENTS

| 4,562,843 | A | * | 1/1986 | Djordjevich et al. | ......... 600/485 |
|---|---|---|---|---|---|
| 5,549,109 | A | | 8/1996 | Samson et al. | |

(Continued)

FOREIGN PATENT DOCUMENTS

| JP | 2004/248793 A | 9/2004 |
|---|---|---|
| JP | 2005/507724 A | 3/2005 |

(Continued)

OTHER PUBLICATIONS

Michard et al., Relation between Respiratory Changes in Arterial Pulse Pressure and Fluid Responsiveness in Septic Patients with Acute Circulatory Failure, Am J Respir Crit Care Med vol. 162. pp. 134-138, 2000.*

(Continued)

*Primary Examiner* — Jim Ketter
*Assistant Examiner* — Reza Ghafoorian
(74) *Attorney, Agent, or Firm* — Nixon Peabody LLP

(57) ABSTRACT

A hemodynamic monitor including a processor incorporating software arranged to continuously analyze and process a blood pressure or arterial volume/plethysmographic signal obtained from the subject in order to derive a plurality of complementary parameters throughout the monitoring of the subject. The monitor also incorporates a display arranged to interact with the processor to display images representing the derived plurality of complementary parameters. The images include at least one image representing graphically at least one stress related hemodynamic parameter plotted against time and at least one image representing graphically at least one fluid responsiveness parameter plotted against time.

14 Claims, 5 Drawing Sheets

(51) Int. Cl.

| | |
|---|---|
| A61B 5/0215 | (2006.01) |
| A61B 5/022 | (2006.01) |
| A61B 5/024 | (2006.01) |
| A61B 5/029 | (2006.01) |
| A61B 5/0402 | (2006.01) |
| A61B 5/145 | (2006.01) |

(56) References Cited

U.S. PATENT DOCUMENTS

| | | | |
|---|---|---|---|
| 6,221,012 B1 | 4/2001 | Maschke et al. | |
| 6,754,608 B2 | 6/2004 | Svanerudh et al. | |
| 6,788,967 B2 | 9/2004 | Ben-Haim et al. | |
| 2005/0154422 A1* | 7/2005 | Band et al. .................. | 607/17 |
| 2006/0111641 A1 | 5/2006 | Manera et al. | |
| 2007/0060822 A1* | 3/2007 | Alpert et al. ............... | 600/481 |
| 2007/0270669 A1 | 11/2007 | Parnagian | |

FOREIGN PATENT DOCUMENTS

| | | |
|---|---|---|
| JP | 2005/529396 A | 9/2005 |
| JP | 2008/531209 A | 8/2008 |
| WO | WO/2003/038566 A2 | 5/2003 |
| WO | 2004/074966 A2 | 9/2004 |
| WO | 2006/000926 A1 | 1/2006 |
| WO | 2007/060559 A2 | 5/2007 |

OTHER PUBLICATIONS

Tavernier et al., Systolic pressure variation as a guide to fluid therapy in patients with sepsis-induced hypotension, Anesthesiology, 1998; 89:1313-21.*

European Patent Office Communication dated Apr. 14, 2008, which includes the European Search Report for corresponding European Patent Application No. 07254032.1, having a completion date of Mar. 13, 2008.

Pearse, Rupert M., Ikram, Kashif, and Barry, John, "Equipment Review: An Appraisal of the LiDCO plus Method of Measuring Cardiac Output", Critical Care, Jun. 2004, vol. 8, No. 3, pp. 190-195.

Anonymous—"LiDCO plus: Continous Real-Time Cardiovascular Monitoring", LiDCO Brochure, Dec. 10, 2007; Retrieved from the Internet: URL:http://lidco-ir.co.uk/docs/Brochure.pdf (retrieved on Mar. 12, 2008).

Reuter, Daniel A., M.D. et al, "Usefulness of Left Ventricular Stroke Volume Variation to Assess Fluid Responsiveness in Patients with Reduced Cardiac Function", Crit. Care Med., 2003, vol. 31, No. 5, pp. 1399-1404.

Jonas, M. et al, "Haemodynamic Optimisation of the Surgical Patient Revisited", Anaesthesia International, Spring Mar. 2008, vol. 2, No. 1.

Photograph of Monitor Screen I, available at least as of Dec. 31, 2004.

Photograph of Monitor Screen II, available at least as of Dec. 31, 2004.

Anonymous—Picco: Intelligentes Diagnose—and Therapiemanagment Zukunftsweisendes Monitoring zum Whole des Patienten, Technologie Broschure, May 23, 2007; Retrieved from the Internet: URL: http://www.pulsion.de/fileadmin/pulsion_share/Products/PiCCO/PiCCO_Brosch_re_d_R02_MPI810200_110906.pdf> (retrieved on Mar. 11, 2008) (English translation attached).

International Search Report corresponding to International Patent Application Serial No. PCT/GB2008/003435, European Patent Office, dated Apr. 21, 2009; (6 pages).

Berkenstadt H et al "Stroke vol. variation as a predictor of fluid responsiveness in patients undergoing brain sugary." Anesthesia and Analgesia Apr. 2001, vol. 92, No. 4, Apr. 2001 pp. 984-989.

Cannesson Maxime et al: "Relation between reptratory variations in pulse oximetry plethysmographic waveform amplitude and arterial pulse pressure in ventilated patients" Critical Care, Biomed Central Ltd., London, GB, vol. 9, No. 5, Aug. 23, 2005.

Michard Frederic: "Changes in arterial pressure during mechnical ventilation." Anesthesiology Aug. 2005, vol. 103, No. 2, Aug. 2005.

Pinsky Michael R: "Probing the limits of arterial pulse non-patent contour analysis to predict preload responsiveness." Anesthesia and Analgesia May 2003, vol. 96, No. 5. May 2003, pp. 1245-1247.

* cited by examiner

PATIENT MONITORING

CROSS-REFERENCE TO RELATED APPLICATIONS

This application is a continuation-in-part of U.S. application Ser. No. 12/099,411, filed on Apr. 8, 2008, which claims the benefit under 35 U.S.C. §119(e) to U.S. Provisional Application No. 60/960,720, filed on Oct. 11, 2007; the contents of which related applications are incorporated herein by reference in their entireties.

FIELD OF THE INVENTION

The present invention relates to improvements in patient monitoring and directing treatment. In particular, the invention relates to apparatus and methods for determining the requirement for, and/or if required the nature or extent of, and/or for monitoring the response to, an intervention by a carer for a subject in order to improve the hydration level and/or hemodynamic status of the subject. The apparatus and methods are particularly useful during a period or periods of hemodynamic instability, such as during a surgical procedure for example.

BACKGROUND OF THE INVENTION

Hemodynamic monitoring is useful in the care of patients, for example in the intensive care unit (ICU) or during surgery. The ICU provides a place for monitoring and care of patients with potentially severe physiological instability requiring advanced artificial life support. Within this context, hemodynamic monitoring is used to identify hemodynamic instability and its cause and monitor the response to therapy. Medical technological advances have enabled monitoring, display, and assessment of many physiological variables (Pinsky M R and Payen D, Crit. Care 2005, 566-572), yet the utility of some aspects of hemodynamic monitoring is unproven. It is the commonly available technologies where clinical studies have demonstrated relevance in terms of improved patient outcome. Physiological measures available from commonly available monitoring devices are given in Table 1.

Table 1. Hemodynamic Monitoring Defined Primary Hemodynamic Variables
A. Non-Invasive Monitoring
1. Electrocardiogram (ECG)
Heart rate, dysrhythmnias, heart rate variability
2. Pulse Oximetry
$SPO_2$, heart rate
3. Arterial Pressure
   Sphygmomanometer
      Systolic and diastolic arterial pressure, heart rate, pulsus paradoxus
4. Central Venous Pressure
Jugular venous distention, hepato-jugular reflux, cannon waves (A-V dissociation).
B. Invasive Monitoring
1. Arterial Catheterization
Systolic, diastolic and mean arterial pressure, heart rate, pulse pressure
Arterial pressure waveform analysis
Stroke volume and cardiac output, pulse pressure variation, systolic pressure variation and stroke volume variation
2. Central venous catheterization
Central venous pressure, venous pressure waveform ("v" waves), respiratory variations
   Thermodilution indices (when coupled to an arterial thermal sensor)
Stroke volume and cardiac output, intrathoracic blood volume, global end-diastolic volume and oxygen delivery ($DO_2$)
3. Pulmonary Artery Catheter
Systolic, diastolic and mean pulmonary arterial pressure, pressure waveform ("v" waves), pulmonary artery occlusion pressure
Mixed venous blood gas analysis—SvO2
Thermodilution cardiac output (by thermodilution either intermittent or continuous)
Stroke volume and cardiac output, RV ejection fraction and RV end-diastolic volume
4. Esophageal Doppler Monitoring
   Stroke volume, cardiac output and stroke volume variation, flow corrected time interval Despite the many options available, most ICUs predominantly monitor and display only blood pressure, heart rate (HR) and pulse oximetry (SpO2). LIDCOplus is a hemodynamic monitor produced by LIDCO Group Plc. The version 4 software for this monitor allows a user to select some specific hemodynamic parameters for display on a shortened time basis. This short term user scalable display is superimposed over the background general trend data and while useful thus obscures sections of the trend data. Improved displays are required which are more appropriate to the requirements of maintaining the hemodynamics of a patient.

SUMMARY OF THE INVENTION

The invention relates to improved hemodynamic monitors. In particular, the invention relates to monitors which provide the carer for a subject with readily interpretable data to improve interventions aimed at restoring the hemodynamic status of the subject.

Thus, according to a first aspect there is provided a hemodynamic monitor for determining the requirement for, and/or if required the nature or extent of, and/or for monitoring the response to, an intervention by a carer for a subject in order to improve the hydration level and/or hemodynamic status of the subject during a period or periods of hemodynamic instability comprising:

(a) a processor comprising software arranged to continuously analyse and process at least a blood pressure or arterial volume/plethysmographic signal obtained from the subject in order to derive a plurality of complementary parameters throughout the monitoring of the subject (b) display means displaying images representing the derived plurality of complementary parameters, characterised in that the images comprise:

(1) at least one image representing graphically at least one stress related hemodynamic parameter plotted against time to provide an early/immediate indication of a change in the hemodynamic status (of the subject) and thus the requirement for an intervention (2) at least one image representing graphically at least one fluid responsiveness parameter plotted against time to provide an indication of the hydration level and associated ventricular pre load status (of the subject) to determine the nature or extent of the intervention if required, wherein the intervention comprises a change in hydration level and/or use/change of any other therapeutic administered to influence the hydration and/or hemodynamic status of the subject (where the intervention may include modulating hydration level and/or modulating any other therapeutic administered to influence the hydration and/or hemodynamic status of the subject, and "modulating" may include initiating administration of a therapeutic or changing administration of a therapeutic).

The hemodynamic monitors of the invention may be further characterised in that the images comprise at least one image representing graphically at least one response related parameter compared to, or generated by, a comparison with the value of the parameter at the point of the intervention to provide an indication of the desired and/or actual response of the subject to an intervention.

The monitors of the invention thus facilitate continuous monitoring of a subject, preferably in real-time, to improve interventions aimed at recovering or restoring hydration or hemodynamic status of the subject. This provides a number of clinical benefits including early and fast warning of changes, a clear indication of the therapeutic route (use of fluid or drugs to restore hemodynamic status) and more effective control of therapy and quantification of hemodynamic response. This contributes to reduce morbidity and post-operative complications (especially infections), reduced length of stay of patients and reduced overall cost of care.

Traditionally, hemodynamic monitors have displayed certain parameters, in particular stress and/or fluid responsiveness and/or short term displays of response related parameters solely as numerical values. Alternatively, hemodynamic monitors have relied upon raw analogue signals. The graphical presentation of these derived parameters by the monitors of the invention provides an improved user interface since changes in the parameter over time, both in the immediate/short term (acute) and longer term (minutes or hours) can be readily observed with minimum or preferably no direct input, manipulation or configuration required from the user.

Moreover, the display of a response related parameter, which may be a simple (numerical) indicator and may be plotted with reference to the value of the parameter at the point of intervention (and in particular plotted relative to a baseline value of the parameter at the point of intervention), provides a particularly intuitive and clear parameter for determining whether an intervention (of the type described herein) provides the desired effect. In one embodiment, the image representing (the value of) this response related parameter (over time) is auto scaled to provide detailed information of the response compared to the baseline. The scales of the axes in the graphical representations of the parameters may be adjustable by the user in certain embodiments.

The monitor incorporates a suitable display, which may be a single screen display, to facilitate ease of viewing by the carer. In particular, the carer may need to respond quickly and accurately to a change in the hemodynamic status of a subject and thus, a single screen displaying the appropriate parameters (as discussed herein) in a readily interpretable fashion is preferred. However, it may be possible for the monitor to incorporate two or more screens if desired. Thus, in specific embodiments related parameters may be present on one screen and a separate set of related or unrelated parameters displayed on a second or further screen. As discussed herein in greater detail, parameters may be grouped as stress related hemodynamic parameters and fluid responsiveness and/or response related parameters respectively. Each set of (at least one) parameters may be displayed on a separate screen. In these embodiments, both or all screens are preferably readily viewable by the carer at the same time. For example, the screens may be positioned parallel to one another within the monitor. Any suitable screen, such as an LCD, plasma or cathode ray tube screen, may be utilised. The screen is preferably a flat screen display. In certain embodiments, the screen is a touch sensitive screen and allows options, such as switching between displays and choosing parameters for display etc. to be selected readily. Touch sensitive screens are commercially available and have the advantage over a keyboard of easy cleaning.

The images displayed on the screens of the invention may be selected and optimised (e.g. length of time for acute and trend displays etc.) by the user to display the most desired parameters, as described herein. It may be possible to switch between the display of different parameters of the same category (as discussed herein) using appropriate functions on the screens in certain embodiments.

Likewise, the display may be a (large) single screen display which incorporates the images of the invention, potentially together with the display of other relevant parameters (such as respiratory parameters for example). In certain embodiments, the images of the invention are displayed in a discrete portion of the display and thus may be readily interpreted and separated from other parameters which may also be displayed. It may also be possible to select the range of parameters presented and the images may be automatically resized according to the number and complexity of the images to be displayed. This is with the proviso that each of the essential parameters as defined herein are always presented to allow improved hemodynamic monitoring. In specific embodiments of the invention, the images which collectively provide improved hemodynamic monitoring are provided in a demarked area of the screen. Preferred arrangements are described herein.

The monitors of the invention are useful for determining the requirement for an intervention by a carer for a subject in order to improve the hydration level and/or hemodynamic status of the subject during a period or periods of hemodynamic instability. Thus, the monitor may be utilised in order to decide whether an intervention is needed in an attempt to restore hydration levels and/or hemodynamic status of the subject. Similarly, the monitors of the invention are useful for assessing the nature or extent of a required intervention made in order to improve the hydration level and/or hemodynamic status of the subject. The monitors of the invention are also useful for monitoring the response to an intervention made in order to improve the hydration level and/or hemodynamic status of the subject in particular by virtue of the display of at least one response related parameter.

The subject is, in a most preferred embodiment, a human subject. The human subject will generally be a hospitalised patient. The patient may be undergoing surgery in specific applications of the invention and the monitor used to determine the requirement for, and/or if required the nature or extent of, and/or monitor the response to, an intervention by an anaesthetist or surgeon. The intervention may be made during the surgery (often a period of a hemodynamic instability) in order to improve the hydration level and/or hemodynamic status of the patient. Interventions made by the surgeon in the act of surgery eg clamping of major blood vessels may interrupt blood flow and/or venous return—which will be detected and displayed by the monitor in order to alert the surgeon to the extent of their impact on the patient's hemodynamics.

Accordingly, the carer is generally a medical practitioner and in specific applications will be the anaesthetist or surgeon carrying out a procedure on the patient. The subject may be hypovolemic and the aim of the intervention to restore circulatory blood volume to normal or acceptable levels, as can be determined by one skilled in the art. Specific targeted patient groups include moderate to high-risk surgery patients, trauma patients requiring resuscitation, step down and high dependency patients with acute circulatory conditions and/or and patients requiring assessment of fluid status and/or screening or assessment of hemodynamic status.

By "a period or periods of hemodynamic instability" is meant one or more periods of time during which the hydration level or hemodynamic status, as indicated by appropriate parameters (as discussed herein), is unstable or deviates from an acceptable or safe level in the subject. Period or periods of hemodynamic instability may occur in a number of circumstances. Non-limiting examples include during surgery, when a subject is suffering from shock (which may be septic, cardiogenic, neurogenic or anaphylactic for example) and under other conditions where there is a loss of cardiac function (such as acute myocardial infarction, cardiomyopathy, congestive heart failure, decreased cardiac output through dehydration or haemorrhage etc., for example). The monitors of the invention may find use most frequently in a variety of settings including: the operating theatre, the intensive care unit, the post operative/intermediate care unit, accident/trauma areas and burn care departments.

The intervention may comprise administration of fluids (such as fluid boluses) to the subject/patient and/or administration of a therapeutic agent designed to improve the hemodynamic status or hydration of the subject/patient. Examples of fluids and therapeutics include isotonic, hypo- or hypertonic solutions, such as saline solutions, buffered salt solutions, and solutions containing colloid, ionotropic, chronotropic and vasoactive drugs. The basic aim of the treatment may be to prevent, or more rapidly repay, outstanding oxygen debt.

The monitors of the invention incorporate a processor comprising, consisting essentially of or consisting of software arranged to continuously analyse and process at least a blood pressure or arterial volume/plethysmographic signal obtained from the subject (optionally in combination with other signals as described herein) in order to derive a plurality of complementary parameters throughout the monitoring of the subject. The processor may be a suitably programmed computer, such as an IBM compatible computer (PC) or a Macintosh computer for example. The processor may also incorporate a suitable transducer to convert the blood pressure or arterial volume/plethysmographic signal into an electrical signal. Alternatively, a transducer may be supplied separately and thus does not form part of the monitor unit (of the invention) itself. Thus, the monitors of the invention may be simply connected to an existing patient monitor, providing the isolated pressure analog output. This is typically an analog arterial pressure wave form output. The monitors of the invention may be employed with any suitable pressure transducer. Of course, this existing patient monitor should be checked to ensure it is properly calibrated. There is generally no requirement for the monitor to be directly connected to the patient applied part (such as a pressure transducer). The monitors themselves may, therefore, be considered non-invasive. A simple cable connection will generally suffice. The monitors may cross-check the parameters against the parameters displayed by the existing patient monitor. If the parameters derived by the monitors of the invention fall significantly outside those calculated by the existing patient monitor—for example are not within approximately 2, 3, 4, 5 up to 10% etc of the values displayed by the existing patient monitor—the monitors of the invention may permit appropriate (manual) adjustments to be made. The monitors may provide a suitable warning of this fact, such as a visual or audible signal for example. Alternatively, the monitor may automatically adjust to take account of any variation in certain embodiments. For example, heart rate thresholds may be increased or decreased as required.

The blood pressure or arterial volume/plethysmographic signal may be obtained from the subject through invasive or non-invasive means. These invasive or non-invasive means may form part of the monitors of the invention in one embodiment. Blood pressures which are measured may be selected from arterial, pulmonary arterial, left atrial, right atrial, aorta, brachial artery, femoral artery, axial artery, pedal artery and radial artery pressures. Preferred invasive means comprise, consist essentially of or consist of a catheter. Suitable catheters are commercially available from a number of medical device suppliers including: Hospira, Becton Dickinson, Arrow, Edwards Lifesciences and Medex and are in routine use in the clinic. Many non-invasive blood pressure monitors are available, such as the Vasotrac monitor (Medwave, Inc.) the Finometer PRO and MIDI, Portapres (Finapres Medical Systems) and the T-Line Tensymeter (Tensys Medical, Inc.).

The monitors of the invention also incorporate display means displaying images representing the derived plurality of complementary parameters. The display means interacts with, and is connected to, the processor such that images are displayed which comprise, consist essentially of or consist of, firstly, in certain embodiments at least one image representing graphically (the change in) at least one stress related hemodynamic parameter plotted against time on the display means to provide an early/immediate indication of a change in the hemodynamic status and thus the requirement for an intervention. As discussed herein these parameters may also be employed to provide an indication of the desired and/or actual response of the subject to an intervention. The plot of the parameter against time may be any suitable plot, such as a line graph or bar chart for example. This portion of the display thus provides an early warning of the requirement for an intervention through readily comprehensible graphic indications of stress related hemodynamic parameters. The value of the relevant parameter as calculated by the processor portion of the monitor is plotted against time to provide a graphical indicator which can be presented over a period of time or continuously as a plot. Parameters may be derived on a continuous beat-to-beat basis. The display may be updated on a continuous basis likewise, or at any suitable time interval such as every 1, 2, 5, 10, 20, 30 seconds etc.

By "stress related hemodynamic parameter" is meant a parameter that alters detectibly and rapidly as a (direct) consequence of the subject being under conditions of stress. These parameters may also be considered as "hemodynamic trend parameters". In preferred but non-limiting embodiments, the at least one stress related hemodynamic parameter plotted against time is selected from mean arterial pressure, systolic pressure, diastolic pressure, heart rate, stroke volume, cardiac output, systemic vascular resistance, respiratory changes in pressure or stroke volume, oxygen delivery, oxygen extraction (see WO 2006/092624) and related parameters indexed to take account of the body surface area of the subject. These parameters can be derived from at least the blood pressure or arterial volume/plethysmographic signal by any suitable means, optionally in combination with other sources of cardiac output and/or stroke volume data, for example derived from a pulmonary artery thermodilution catheter, impedance measurements, Doppler ultrasound and Fick approaches. Many algorithms are known for deriving the appropriate stress-related parameters. Particularly useful parameters include stroke volume, cardiac output and systemic vascular resistance. Also particularly useful are respiratory variations in pulse pressure and stroke volume. These parameters, displayed beat to beat can be advantageously displayed with trend changes of pulse pressure variation and stroke volume variation respectively, as discussed in greater detail herein.

Mean arterial pressure is the average arterial pressure during a (single) cardiac cycle and is generally measured in units of mm Hg. As discussed above, which discussion applies mutatis mutandis, mean arterial pressure may be measured using any suitable either invasive or non-invasive means.

Systolic pressure is the peak arterial pressure during systole. Again, it is typically measured in units of mm Hg and may be measured using any suitable either invasive or non-invasive means, as discussed above.

Diastolic pressure is the lowest arterial pressure measured during the cardiac cycle (at the end of diastole—the relaxation of the heart). Again, it is typically measured in units of mm Hg and may be measured using any suitable either invasive or non-invasive means, as discussed above. Mean arterial pressure may be derived from the systolic and diastolic pressures.

Heart rate is generally calculated as the number of contractions of the heart in one minute and is therefore typically expressed in units of beats per minute (bpm). Thus, the change in heart rate over each beat may be plotted to form an image for display by the monitors of the invention. Heart rate can be measured by any suitable means, in particular through standard invasive or non-invasive means. Preferred invasive means include a catheter. Preferred non-invasive means include electrocardiographic monitoring of the heart (ECG) or use of a pulse oximeter. Commercially available heart rate monitors (which also rely upon electrocardiography) may also be utilised as appropriate. Heart rate may be derived from the arterial blood pressure waveform for example, using an autocorrelation method as described in WO97/24982, Fourier analysis, filtering techniques on the pressure waveform and/or edge detection or any other suitable technique. Reference can be made to EP0994672 (LIDCO Group Plc) in this regard.

Stroke volume is the amount of blood pumped by the left ventricle of the heart in one contraction and is generally expressed in units of ml. Stroke volume is related to the cardiac output and heart rate of the heart. Stroke volume may be calculated by any known means and is often derived from blood pressure measurements taken from a patient. Stroke volume is preferably derived from the arterial blood pressure waveform for example, using an autocorrelation method as described in WO 97/24982, Fourier analysis, filtering techniques on the pressure waveform and/or edge detection or any other suitable technique. Reference can be made to EP0994672 (LIDCO Group Plc) in this regard wherein stroke volume is derived from the arterial pressure waveform by:
(i) recording and storing the arterial blood pressure waveform of a patient from a blood pressure monitoring device over a period of time;
(ii) subjecting the data obtained in step (i) to Fourier analysis in order to obtain the modulus of the first harmonic; and
(iii) determining the nominal stroke volume from the modulus of the first harmonic obtained in step (ii) and data relating to the arterial blood pressure and the heart rate.

Stroke volume (by virtue of its relationship to cardiac output) may be estimated by the commercially available PULSECO algorithm. This software can calculate continuous beat-to-beat stroke volume, stroke volume variation (SVV) and cardiac output by analysis of the arterial blood pressure trace following calibration with an indicator dilution cardiac output measurement (using the LIDCO system—see WO93/09427). The lithium dilution calibration process allows determination of the actual value of the maximum arterial volume (Vmax) for a particular patient. The monitors of the invention may utilise a nomogram which creates an estimate for Vmax that is used to scale the PULSECO algorithm for an individual patient in certain embodiments. This may provide an estimate of stroke volume whilst allowing simple and rapid set-up (since the requirement for calibration is removed). The nomogram is a digital nomogram and may comprise look up tables or curves or appropriate mathematical equations as appropriate. Calibration may, however, be utilised where appropriate—for example where critically ill patients are concerned. Accordingly, the monitors of the invention may permit entry of an actual cardiac output value—achieved using any suitable technique—in preference to a nominal value as desired. This may apply to all suitable parameters calculated and/or displayed by the monitors of the invention. Manual calibration using a known cardiac output value should be carried out during a hemodynamically stable period with minimal variation in blood pressure and heart rate and should be entered promptly to avoid bias due to a change in the patient's condition.

Cardiac output is the volume of blood pumped by the heart over a period of time. It is generally measured in 1/min and is equal to heart rate multiplied by stroke volume. Cardiac output may be measured using LIDCO's PULSECO system, which is commercially available. Here, cardiac output is derived through running the PULSECO System as an algorithm within the LIDCOplus Monitor. Nomograms may be employed, as discussed and defined above as a means of estimating cardiac output as an alternative to manual calibration. In one embodiment, cardiac output is determined by the methods described in EP0920278 (LIDCO Group Plc) which in general terms comprise, consist essentially of or consists of the steps of:
(i) recording and storing the arterial blood pressure waveform of a patient from a blood pressure monitoring device over a period of time;
(ii) subjecting the waveform obtained in step (i) to a non-linear transformation that corrects for the variation of the characteristics of the arterial system with pressure;
(iii) subjecting the corrected waveform from step (ii) to autocorrelation in order to derive the pulsatility and heart rate of the corrected waveform;
(iv) calculating the nominal stroke volume from the pulsatility; and
(v) obtaining the nominal cardiac output by multiplying the nominal stroke volume by the heart rate.

In another embodiment, cardiac output is determined by the methods described in EP0994672 (LIDCO Group Plc) which in general terms comprise, consist essentially of or consists of the steps of:
(i) recording and storing the arterial blood pressure waveform of a patient from a blood pressure monitoring device over a period of time;
(ii) subjecting the data obtained in step (i) to Fourier analysis in order to obtain the modulus of the first harmonic;
(iii) determining the nominal stroke volume from the modulus of the first harmonic obtained in step (ii) and data relating to the arterial blood pressure and the heart rate; and
(iv) obtaining the nominal cardiac output from data obtained in step (iii).

Systemic vascular resistance (SVR) is the resistance to blood flow offered by the systemic vasculature. SVR can be calculated by dividing mean arterial pressure by cardiac output. Accordingly, SVR may be measured using LIDCO's PULSECO system which is commercially available. In a preferred embodiment, cardiac output is determined by the methods described in EP0920278 or EP0994672 (both LIDCO Group Plc), the essential steps of which are set forth above.

Oxygen delivery ($DO_2$) is another useful stress related parameter and reflects oxygen quantities made available to the body. $DO_2$ may be calculated from cardiac output (CO), arterial oxygen saturation and haemoglobin concentration in the blood. A typical calculation is:

$$DO_2 = CO \times (SaO_2 - SvO_2) Hb \times 1.36 \text{ ml } O_2/\text{min}/m^2$$

Where
$SaO_2$=arterial oxygen saturation (%)
$SvO_2$=mixed venous oxygen saturation (%)
Hb=haemoglobin concentration (gm/dl)

$DO_2$ may be measured by any suitable means. Pulse oximeter oxygen saturation ($SpO_2$) provides an estimate of $SaO_2$. Suitable pulse oximetry apparatus includes the Propac Encore Monitor (Beaverton, USA), Masimo SET and Rainbow SET Oximeter series (Masimo, Inc. Irvine, USA), Oximax Pulse Oximetry System (Nellcor, Pleasonton, USA) and the NONIN and BCI pulse oximeters (Harrell Medical, Inc, USA). $SvO_2$ may be measured through any suitable means, such as using a pulmonary artery catheters and fibreoptic oximetry.

All of the relevant parameters described herein may (where appropriate) be indexed, if required or desired, to take account of the body surface area of the subject. Body surface area (BSA) of a subject is typically calculated from the height and weight of the subject and expressed in $m^2$. Examples of indexed parameters which may be useful in the present invention include cardiac index (CI) which equals CO divided by BSA ($1/\text{min}/m^2$), stroke index (SI) which equals SV divided by BSA ($ml/m^2$) and oxygen delivery index ($DO_2I$) which equals $CI \times (SaO_2 - SvO_2) Hb \times 1.36 \text{ ml } O_2/\text{min}/m^2$ (where $SpO_2$ can be substituted for $SaO_2$ as desired).

The display means interacts with the processor such that images are displayed which comprise, consist essentially of or consist of secondly, in certain embodiments at least one image representing graphically (the change in) at least one fluid responsiveness parameter plotted against time to provide an indication of the hydration level and/or associated ventricular pre load status of the subject. In some embodiments the parameters may also be useful to indicate the desired and/or actual response of the subject to an intervention. The plot of the parameter against time may be any suitable plot, such as a line graph or bar chart for example. As discussed herein the intervention preferably comprises, consists essentially of or consists of a change in hydration level and/or the use of and or change in the levels of any other therapeutic administered to influence the hydration and/or hemodynamic status of the subject (where the intervention may include modulating hydration level and/or modulating any other therapeutic administered to influence the hydration and/or hemodynamic status of the subject, and modulating, may include initiating administration of a therapeutic or changing administration of a therapeutic).

Thus, the "at least one fluid responsiveness" parameter is a parameter that provides a useful indication of the hydration and/or hemodynamic status of the subject. In particularly preferred, but non limiting, embodiments the at least one fluid responsiveness parameter plotted against time is selected from stroke volume variation (SVV), pulse pressure variation (PPV), systolic pressure variation (SPV), mean blood flow during a passive leg raising procedure (PLR) and pulse oximetry plethysmographic (POP) waveform amplitude. SVV and/or PVV are particularly useful fluid responsiveness parameters in the context of the invention. In certain embodiments of the invention, separate fluid responsiveness and response related parameters are presented in the same display. Absolute or relative (percentage) changes may be displayed as appropriate (as discussed herein).

Generally, these parameters provide an indication of pre-load-responsiveness and accordingly, any parameter providing a reliable indication of preload-responsiveness may be utilised. The parameters utilised may provide an indication of whether the subject is hypovolemic and therefore requires an intervention and/or provide an indication if and when the intervention has been successful in restoring blood volume in the subject. Means for calculating these parameters are known in the art and any suitable means may be implemented in the monitors of the invention.

Stroke volume variation is the variation in (left ventricle) stroke volume and is generally quantified as the percentage change between the maximal and minimal stroke volume (SV) values divided by the average of the minimum and maximum SV over a defined time interval. Typical time intervals are between around 10, 20 or 30 seconds and 40, 50 or 60 seconds or around two or three to five breaths for example. A representative target zone (as discussed herein) for SVV may be around 10% since SVV tends to predict fluid responsiveness when the values are consistently above 10%. PULSECO software calculates SVV in specific embodiments.

Pulse pressure is the change in blood pressure during contraction of the heart and is often calculated as systolic pressure minus diastolic pressure. Pulse Pressure Variation (PPV) is the variation in pulse pressure over time and is generally quantified as the percentage change between the maximal and minimal pulse pressure values divided by the average of the minimum and maximum pulse pressures over a defined time interval. Typical time intervals are between around 10, 20 or 30 seconds and 40, 50 or 60 seconds or around two or three to five breaths for example. A representative target zone (as discussed herein, which discussion applies mutatis mutandis) for PVV may be around 13%. As the PVV goes above 13%, it becomes more likely that the patient will respond to fluids.

Systolic pressure variation (SPV) is the variation in systolic pressure over time and is generally quantified as the change between the maximal and minimal systolic pressure values divided by the average of the minimum and maximum systolic pressures over a defined time interval. Typical time intervals are between around 10, 20 or 30 seconds and 40, 50 or 60 seconds or around two or three to five breaths for example. SPV and PPV are related parameters, although PVV may in certain circumstances prove more useful because it takes into account positive pleural pressure on the aorta (since it effects the systolic and diastolic pressures to the same degree) (Michard et al., Am J Respir Crit Care Med 2000; 162:134-138).

Another useful preload responsiveness parameter is mean blood flow during a passive leg raising procedure (PLR). PLR is a simple reversible manoeuvre that mimics a rapid fluid loading. It transiently and reversibly increases venous return by shifting venous blood from the legs to the intrathoracic compartment (Lafanechere et al., Critical Care 2006, 10:R132 and references cited therein). Mean blood flow may be measured by any suitable means, such as through use of Esophageal Doppler (ED) for example as discussed herein. Devices for obtaining ED measurements are known in the art and commercially available, such as the Hemosonic 100 device (Arrow Intl, USA) and the CardioQ (Deltex, Chichester, UK).

In certain embodiments, the at least one fluid responsiveness parameter comprises, consists essentially of or consists of pulse oximetry plethysmographic (POP) waveform amplitude. A relationship has been shown between the POP waveform and respiratory variation in arterial pulse pressure (Cannesson et al., Critical Care 2005, 9: R562-568).

As aforementioned, the display means may interact with the processor such that images are displayed which comprise, consist essentially of or consist of at least one image representing graphically at least one response related parameter. The response related parameter may be displayed as a value compared to the value of the parameter at the point/time of the intervention to provide an indication of the desired and/or actual response of the subject to an intervention.

The at least one response related parameter may be plotted against time with reference to an indication of the value of the parameter at the point of the intervention. The plot of the parameter against time may be any suitable plot, such as a line graph or bar chart. In a specific embodiment, the at least one response related parameter may be plotted against time relative to a baseline value of the parameter taken at the point of the intervention. Alternatively or additionally, the at least one response related parameter is indicated as the absolute or percentage change compared to the value of the parameter at the point of the intervention. This may be indicated as a simple numerical indicator for example (which may be "plus" or "minus" depending upon whether the value of the parameter has gone up or down following the intervention).

As discussed herein the intervention preferably comprises, consists essentially of or consists of a change in hydration level and/or the use of and or change in the levels of any other therapeutic administered to influence the hydration and/or hemodynamic status of the subject. The intervention may include modulating hydration level of the subject and/or modulating any other therapeutic administered to influence the hydration and/or hemodynamic status of the subject. The term "modulating," as used herein, may include initiating administration of a therapeutic or changing administration of a therapeutic.

Thus, the "at least one response related parameter" is a parameter that is altered reliably in response to and/or is directly influenced by the intervention, preferably substantially immediately, to provide a readily perceivable indication of the response of the subject to the intervention. As discussed herein, response related parameters may be indicated relative to a "baseline", which is preferably the value of the response related parameter at the point of the intervention. Use of a baseline value at the point of intervention against which a response related parameter may be plotted provides particularly readily identifiable information to the clinician/carer to confirm that the intervention is producing a (beneficial) response in the subject. The plot is scaled (in particular on the y axis) and may be auto scaled to provide detailed information on the change in the parameter as time from the intervention progresses. The point of intervention, or indeed any other "event" of relevance may be marked graphically by the monitor on the images presented by the monitor. Where multiple events, such as interventions, occur each may be marked and identified individually (for example through use of appropriate numbering, lettering or colour schemes). As discussed herein, the event may begin display of an appropriate parameter in a suitable "event response" window. The same event may also be marked on the other windows displaying stress related homodynamic parameters) and/or fluid responsiveness parameter(s).

The monitors may alter permit the user to provide a suitable annotation of the interventions. Appropriate menus and submenus may be presented allowing the user to readily store this information for review and analysis at a later time.

The "event response" window may be stopped or reset by the user as required, such as when a further intervention takes place. Each event may create a separate mark to note the fact.

In further embodiments, the response related parameter is the same parameter as one of the stress related parameters or fluid responsiveness parameters. In these embodiments, the response related parameter may or may not be plotted in a separate image. In one embodiment, the response related parameter is displayed in the same image as the stress related and/or fluid responsiveness parameter. This may be achieved by providing an indication, for example through appropriate marking, on the plot of the stress related and/or fluid responsiveness parameter the point/time of intervention. An appropriate marking may comprise an arrow or line or other suitable visual indicator. This may be done automatically by the software or may be done manually by the user (for example through appropriate interaction with the touch screen). By indicating the point of intervention on the plot of the stress related and/or fluid responsiveness parameter the value of the parameter at this time point is readily decipherable. The plot of the parameter following this time point then provides a graphical representation of the response related parameter over time. In specific embodiments, this plot is combined with a further indication of the overall change in the parameter following the intervention. This may be a single identification, such as a numerical identification, for example, as discussed herein. The further indication is preferably continuously updated over time relative to the value of the parameter at the point of intervention. The response related parameter and/or the further indication of the response related parameter may be indicated as an absolute or percentage change as appropriate. For the response related parameter plot the nature of the change may be determined by the corresponding changes in the fluid responsiveness and/or stress related parameter.

In certain embodiments, the at least one response related parameter comprises, consists essentially of or consists of one of the stress related parameters and/or fluid responsiveness parameters described herein, but is plotted separately against the baseline value of the parameter at the point of intervention. It may equally be a separate parameter if desired. This parameter is generally presented in a separate image, as described herein, although this may not be essential. The percentage or absolute change in the at least one parameter from the point of intervention may be processed and displayed. In addition to the graphical representation of the change against the baseline over time, it may also be possible to display the percentage or absolute change in the at least one response related parameter since the intervention. This may be done as a numerical value for example. This may facilitate recordation of changes by a user.

Stroke volume and or stroke volume response, in particular percentage or actual stroke volume response, can be measured to provide an indication of the response to the intervention. Thus, this represents a preferred "response related parameter" calculated and displayed by the monitors of the invention. As aforementioned, percentage or actual stroke volume response may be indicated relative to a "baseline" which is preferably the stroke volume at the point of the intervention. Thus, improvements in hemodynamics and/or hydration status following the intervention can be readily determined against the baseline. Other response related parameters comprise, consist essentially of or consist of heart rate, cardiac output, oxygen delivery/consumption, systemic vascular resistance, respiratory variations in stroke volume and pressure and arterial pressure parameters for example. However, as discussed above, the response related parameter may correspond to any one or more of the stress related and fluid responsiveness parameters as appropriate.

It should be noted that all (trending) parameters, as appropriate, may be calculated and utilised as uncalibrated or calibrated values. If uncalibrated, they are designated as nominal values eg nSV.

Thus, the display portion of the monitors of the invention allows the requirement for an intervention to be readily identified through presentation of specifically adapted images facilitating interpretation of the relevant parameters.

In preferred embodiments of the invention, the hemodynamic monitor is further characterised in that the at least one image representing graphically at least one of the parameters, which may be at least one stress-related parameter and/or at least one fluid responsiveness parameter and/or at least one response related parameter incorporates a target zone representing an acceptable value or range of values for the at least one parameter. The acceptable value or range of values of the parameter may be used to indicate that the hydration and/or hemodynamic status of the patient has recovered to normal levels (following the intervention). Suitable values or ranges of values may be selected by one skilled in the art depending upon the parameter. The selected value or values may be adjusted by the user in certain embodiments, once selected. For parameters such as the fluid responsiveness parameters, the target zone may incorporate a desired range of values. The target zone may be one derived independently of the subject being monitored. For example, where stroke volume or pulse pressure variations are expressed in percentage (change) terms, the target zone may be determinable independent of the subject since the variations are relative changes which should be consistent for each subject. For other parameters, in particular stress related parameters such as blood pressure parameters (as described herein) and heart rate, it may be necessary to define the target zone on a subject by subject basis. Here, the target zone may be defined by the value of the parameter at the start of patient monitoring. Thus, for example each individual is likely to have a different heart rate and/or blood pressure parameter and it is desired that the intervention returns the subject to the pre-monitoring level, whatever that level may be. The target zone may take any suitable form to facilitate determination of whether the parameter is within an acceptable range at any given time point during monitoring of the subject. In certain embodiments, the target zone takes the form of a shaded band so that the carer can readily visualize, at a glance, whether the current reading is in, moving towards or away from, a target value or range of values. The shaded band is preferably of a lighter colour than the plot of the parameter against time such that the plot can readily be distinguished from the target zone. A preferred colour is green, to provide a positive indication of the target, although any appropriate colour may be utilised. An alternative target zone may be a bordered box. Audible as well as visual signals may be utilised as appropriate. Where the target zone is a single parameter value or a small range of values, the target zone may be presented as a single line (of appropriate thickness) to readily show when the parameter is approaching or has reached the desired value or values.

The monitors of the invention may be further characterised in that the at least one stress related hemodynamic parameter and/or the at least one fluid responsiveness and/or the at least one response related parameter is displayed in the form of at least one image representing current changes in the parameter in combination with at least one image representing longer term changes in the parameter scaled, and preferably auto scaled, to the duration of monitoring of the subject, or scaled to any representative longer period of time, wherein the at least one image displaying current changes in the parameter is spatially separated from the at least one image representing longer term changes in the parameter and comprises an expanded view of a suitable portion of the auto scaled/longer scaled image thus facilitating monitoring of current changes in the value of the parameter. By "scaled to any representative longer period of time" is meant a longer period than shown in the "current changes" image. This does not necessarily need to be over the entire duration of subject monitoring in all instances but is intended to provide a reliable indication of the overall trend change in the relevant parameter. A maximum window size may be set for the longer term display, such as around 8 or 10 hours for example.

Thus, in effect, there is provided by the display means both a "trend" display and an "acute changes" display for any suitable parameter. These terms are used herein to describe the at least one image representing longer term changes in the parameter auto scaled to the duration of monitoring of the subject, (such as for example to the duration of a medical, such as an operative, procedure) or scaled to any representative longer period of time and the at least one image representing current changes in the parameter, respectively. In particular embodiments, a trend display and acute changes display is presented for at least one stress related hemodynamic parameter and for at least one fluid responsiveness and/or for at least one response related parameter. In further embodiments, a trend display and acute changes display is presented for at least one stress related hemodynamic parameter and for at least one fluid responsiveness and for at least one response related parameter. In certain embodiments trend displays and acute changes displays are presented for a plurality of stress related parameters.

As aforementioned, the at least one image displaying current changes in the parameter is spatially separated from the at least one image representing longer term changes in the parameter. The acute changes displays are spatially separated from the trend displays in order to ensure the respective displays can be viewed and interpreted consecutively or simultaneously without requiring the input of the user. This display combination helps to achieve the overriding goal of the monitors of the invention, namely improving the user interface to facilitate improved interventions by a clinician. Trend displays permit a complete picture of changes and are useful in examining long term changes (increases or decreases) in particular changes since the start of monitoring and/or a particular intervention or other event.

The display may be separated into discrete "panels", with each panel containing an acute changes display or trend display respectively. Preferably, acute change and trend displays for each respective parameter are provided side by side to facilitate viewing and comparisons for each parameter. Thus, the display means may incorporate pairs of acute and trend displays presented in appropriate rows and/or columns. The display may incorporate suitable demarcation as appropriate.

The acute changes display comprises, consists essentially of or consists of an expanded view of a suitable portion of the (auto) scaled/longer scaled image thus facilitating monitoring of current changes in the value of the parameter. In particular, when monitoring hemodynamics of a subject, the carer is often interested in small variations (in percentage terms) in the relevant parameter or parameters. Conventional trend displays may result in oversight of minor but significant changes. The acute changes displays provide an expanded view of the trend display over a (short) period of interest. The processor may automatically rescale the acute changes display to ensure minor changes in the parameter (presented on the y-axis preferably) can be readily visualised. This may equally apply to display of changes in at least one event response parameter against the baseline value to provide maximally sensitive information. The acute changes display may be presented over a short time period, such as 10, 20 or 30 seconds to 40, 50 or 60 up to 120 or more seconds for example, or may present the parameter per beat over a limited number of beats as appropriate. Preferably changes are monitored against a target zone, as described herein (which description applies equally), to further improve the user interface.

Numeric displays of any one or more, up to all parameters displayed according to the invention may accompany the graphical displays. Such numeric displays may update at regular time intervals such as every 1, 2, 5, 10, 20 seconds etc and may also be averaged over similar time periods as required. Where numeric displays are incorporated functionality may be provided to switch these off to view only the graphical trends as desired.

Sensitivity of monitoring may be (further) enhanced through use of multiple complementary stress related parameters. Thus, in specific embodiments, the display means displays images representing graphically a plurality of stress related hemodynamic parameters plotted against time to provide an early/immediate indication of a change in the hemodynamic status and thus the requirement for an intervention. As appropriate (in particular where the units of measurement are comparable or of similar values), complementary stress related parameters may be incorporated into combined images displaying the multiple parameters in the same display. For example, plots of heart rate and mean arterial pressure (or a related blood pressure measurement) or stroke volume and cardiac output against time may be presented in a single display panel, preferably for both acute changes displays and trend displays. Preferably, the individual parameter plots are readily distinguished from one another through use of appropriate colour schemes, shading etc.

Additionally or alternatively, the hemodynamic monitors of the invention may be further characterised in that the display means displays images representing graphically a plurality of fluid responsiveness parameters plotted against time to provide an indication of the hydration level and/or associated ventricular pre load status of the subject. The plurality of parameters may be selected from any suitable parameters, a number of examples of which are described herein. Each parameter may be displayed in a combined or separate image as appropriate, as discussed above for the stress related parameters.

Additionally or alternatively, the hemodynamic monitors of the invention may be further characterised in that the display means displays images representing graphically a plurality of response related parameters plotted over time against the baseline to provide an indication of the desired and actual response of the subject to the intervention. The plurality of parameters may be selected from any suitable parameters, a number of examples of which are described herein. Each parameter may be displayed in a combined or separate image as appropriate, as discussed above for the stress related parameters.

Combinations of fluid responsiveness and response related parameters are preferred. For example, percentage fluid response and SVV (or PPV) and/or SV (or PP) per beat may be displayed in certain embodiments. Complementary parameters may be incorporated into combined images where appropriate, provided that data interpretation does not suffer, although the parameters are generally presented separately.

For the embodiments in which the monitors are characterised in displaying images representing graphically a plurality of stress related hemodynamic parameters plotted against time and/or images representing graphically a plurality of fluid responsiveness and/or images representing graphically a plurality of response related parameters plotted against time, it is preferred that the respective image sets are displayed in defined groupings. The order in which the respective parameters is displayed is of critical importance to ensure that the carer is able to readily interpret the data and thus firstly intervene at the most appropriate juncture and in the most appropriate fashion and secondly monitor and adjust the nature and/or extent of the intervention as appropriate.

In specific embodiments, the hemodynamic monitor is further characterised in that the images representing graphically one or more or a plurality of stress related hemodynamic parameters plotted against time are displayed in an upper portion of the display and the images representing graphically one or more or a plurality of fluid responsiveness and/or plurality of response related parameters (where employed) plotted against time are displayed in a lower portion of the display. If both fluid responsiveness and event response parameters are displayed one may be displayed in the central portion and the other in a lower portion of the display. This separation of the images into discrete upper and lower panels again facilitates rapid interpretation of the presented data by the carer, thus improving intervention. As desired, alternative groupings are possible such as the reverse of the above, or side by side groupings/panels for example.

In still further embodiments, fluid responsiveness parameters may be displayed in a separate grouping or panel from one or more response related parameters, in particular where separate response related parameters are derived and displayed. Thus, the appropriate portion of the display may be split further to separate fluid responsiveness parameters from response related parameters. This may allow the intervention to be monitored together with the overall (percentage) response thereto more readily. In certain embodiments, response related parameters are presented in the lower panel of the display since they represent the intervention related "output" of the monitors of the invention.

In additional embodiments of the invention, applicable to each aspect of the invention the display means may also display one or more images representing raw analogue data received by the processor. Such data may usefully be presented as an indication of the quality of the signal being obtained, analysed and processed by the processor. In specific embodiments, the blood pressure analogue signal obtained from the subject is displayed. The analogue blood pressure signal may be monitored in particular to provide a readily interpretable indication of the signal quality of the output of the left ventricle of the heart. Thus, for example during surgery, manual/mechanical intervention may influence the analogue blood pressure signal obtained from the subject. This would, in turn, influence the derived parameters which are displayed through the display means of the invention. The raw analogue data of the blood pressure signal provides a responsive and easily interpreted indication of left ventricle signal quality and helps to avoid the derived parameters displayed by the monitor being interpreted incorrectly as indicating a significant change in the hemodynamic status of the subject and thus leading to an incorrect intervention. This is particularly pertinent where the surgeon is carrying out a surgical procedure and the anaesthetist is watching the monitor to determine the requirement for, and/or if required the nature or extent of, an intervention. The blood pressure signal display may provide a readily interpretable indication that there has been a temporary, manually/mechanically induced, interference and thus the change in the derived parameters is not necessarily an indication that a fluid based intervention in order to improve hemodynamics of the patient (as discussed herein) is required. Rather, the blood pressure signal display may indicate an alteration/lessening of the mechanical intervention is appropriate to improve/restore the hemodynamics of the subject.

In specific embodiments, the raw analogue data images may partially and/or temporarily replace one or more of the event response parameter displays. For example, in one embodiment, it may be possible to switch between an event response parameter image and a raw analogue data image as required. Thus, for example, pre-intervention it may be desirable to monitor the blood pressure signal to ensure manual/mechanical variation is not influencing the quality of the left heart output signal whereas post intervention it may be desirable to switch to monitoring of an event response parameter, such as fluid responsiveness to determine the effect of the intervention on the subject.

The one or more images representing raw analogue (blood pressure signal) data may be presented in a discrete part of the display in one embodiment. This may, for example, be combined with an indication, such as a numerical indication, of other data such as current systolic and/or diastolic pressure. The images may be suitably scaled or re-scaled, in particular autoscaled, to take account of any short term changes in the relevant parameters outside of the normal ranges.

In specific embodiments of the invention, the display means also displays one or more images providing an indication of the quality of the right heart/venous return signal/preload status. These images are generally images displaying (graphically) respiratory variation in one or more suitable parameters. The suitable parameters may be any of the fluid responsiveness parameters discussed herein, which embodiments apply here mutatis mutandis. In specific embodiments, the pulse pressure variation and/or the stroke volume variation are displayed on a beat by beat basis. This gives an indication of the signal quality of the right (side of the) heart/venous return/preload status.

Thus, for example during surgery, manual/mechanical intervention may influence the right heart/venous return signal/preload status obtained from the subject. This would, in turn, influence the derived parameters which are displayed through the display means of the invention. The display of respiratory variation in the fluid responsiveness parameter provides an indication of the effect of the manual/mechanical intervention. The term "preload" refers to maximum stretch on the heart's muscle fibres at the end of diastolic filling. The degree of stretch is determined by the volume of blood contained in the ventricle at that time, higher volumes of blood result in greater stretch of the myocardial muscle fibres. Greater stretch results in greater contraction of the muscle fibres which increases the stroke volume ejected to the tissues. This relationship between ventricular end-diastolic filling volume and stroke volume is known as Starling's Law of the Heart, which states that the energy of contraction of the muscle is proportional to the pre-contraction length of the muscle fibre.

For the parameters, such as pulse pressure variation and systolic pressure variation, an approximately sinusoidal respiratory variation is expected. This is generally around a value of approximately 10%-15%. It may, however, be normalised to a mean value which results in a percentage value that oscillates around a baseline of zero. A sudden and/or significant deviation from this regular signal within the normal respiratory variation may indicate that the manual/mechanical intervention is strongly influencing the parameters displayed by the monitors of the invention. This in turn may influence the surgery but may not necessarily indicate a significant change in the hemodynamic status of the subject and thus the requirement for a hemodynamic intervention. This is particularly pertinent where the surgeon is carrying out a surgical procedure and the anaesthetist is watching the monitor to determine the requirement for, and/or if required the nature or extent of, an intervention. The respiratory variation display may provide a readily interpretable indication that there has been a temporary, manually induced, interference and thus the change in the derived parameters is not necessarily an indication that some form of intervention in order to improve hemodynamics of the patient (as discussed herein) is required. The images may be suitably scaled or re-scaled, in particular autoscaled, to take account of any short term changes in the relevant parameters outside of the normal ranges.

Since the parameters are generally fluid responsiveness parameters, they will typically be displayed in an appropriate location on the screen with any other fluid responsiveness parameters which are displayed (perhaps on a different time scale for example, rather than on a beat by beat variation). Thus, the fluid responsiveness portion of the display may incorporate both respiratory variation images and longer term variation images as appropriate. These may rely upon systolic pressure variation and/or pulse pressure variation for example.

The respiratory variation in the at least one (fluid responsiveness) parameter may be the same as the image representing current changes in the at least one fluid responsiveness parameter described herein. Beat by beat changes represent current variations in the parameter which can be contrasted with a longer term trend display of the same parameter. The respiratory variation may (additionally) be displayed numerically, optionally together with another parameter such as heart rate variation. This is relevant because if heart rate variation (HRV) exceeds 10%, SVV and PVV values may be considered unreliable. If HRV exceeds 10% this may be indicated visually, such as by a change of colour, or audibly or through any other means.

Additionally, the "short term view" or acute changes display of respiratory variation in the fluid responsiveness parameter (SV or PV per beat) is useful to both set ventilator parameters and to wean the patient off the breathing machine (by wean is meant to gradually reduce ventilatory support). On set-up of the ventilator the machine is set to a specific tidal volume, a volume in mls/kg that the ventilator is applying to the patient's breathing circuit per ventilatory cycle (breath size). This may be set around 6-12 mls/kg body mass. Higher levels can excessively retard venous return to the heart but may be required to obtain full perfusion to/of the lungs. The tidal volume can be optimally adjusted by looking at the short term or acute changes display of respiratory variation in Stroke Volume or Pulse Pressure and ensuring that the tidal volume applied is not excessively obstructing venous return, which would be seen as an increased amplitude in the breath to breath variation in PPV % or SVV %. Alternatively, if a high tidal volume is required for lung perfusion then more fluids can be given to improve venous return. The short term display of respiratory variation in Stroke Volume or Pulse Pressure will thus help to balance tidal volume and fluid volume. Equally, if the patient is excessively full (for example as shown in the trend display in FIG. 4) then weaning (ie reducing the tidal volume) will reduce the ventilator break to venous return and may result in excessive fluid being returned to the heart resulting in pulmonary overload and failure to wean. Accordingly, the circulating fluid volume can be reduced by administration of a diuretic and weaning slowed until the fluid status is less likely to cause problems.

The respiratory variation display is thus extremely useful and represents a novel approach in hemodynamic monitoring, in particular in combination with a display of longer term changes (trend display) of the same/complementary fluid responsiveness parameter plotted over a period of time (as opposed to beat by beat). Thus, in one aspect the invention provides a hemodynamic monitor and corresponding method for determining the requirement for, and/or if required the nature or extent of, and/or for monitoring the response to, an intervention by a carer for a subject in order to improve the hydration level and/or hemodynamic status of the subject during a period or periods of hemodynamic instability comprising:

(a) a processor comprising software arranged to continuously analyse and process at least a blood pressure or arterial volume/plethysmographic signal obtained from the subject in order to derive a plurality of complementary parameters throughout the monitoring of the subject (b) display means displaying images representing the derived plurality of complementary parameters, wherein the images comprise at least one image representing graphically the respiratory variation in at least one fluid responsiveness parameter plotted against time. As discussed herein, this fluid responsiveness parameter is generally pulse pressure or stroke volume and thus the beat to beat variation in these parameters can be displayed by the monitors of the invention. These monitors and methods may incorporate any additional embodiment of the invention discussed herein, as appropriate. In particular, the respiratory variation is typically presented together with at least one image representing graphically the fluid responsiveness parameter plotted against time to provide an indication of the hydration level and associated ventricular pre load status of the subject (especially SVV or PVV).

This combination helps to determine the nature or extent of the intervention if required, with the trend display indicating if fluids are needed and the respiratory variation (acute changes) display also assisting in this regard and providing data regarding signal quality. This may be combined with additional signal quality indicators as desired.

Similarly, the invention also provides a hemodynamic monitor for determining the requirement for, and/or if required the nature or extent of, and/or for monitoring the response to, an intervention by a carer for a subject in order to improve the hydration level and/or hemodynamic status of the subject during a period or periods of hemodynamic instability comprising:

(a) a processor comprising software arranged to continuously analyse and process at least a blood pressure or arterial volume/plethysmographic signal obtained from the subject in order to derive a plurality of complementary parameters throughout the monitoring of the subject (b) display means displaying images representing the derived plurality of complementary parameters, characterised in that the images comprise:

(1) at least one image representing graphically at least one stress related hemodynamic parameter plotted against time to provide an early/immediate indication of a change in the hemodynamic status and thus the requirement for an intervention (2) at least one image representing graphically at least one fluid responsiveness parameter plotted against time to provide an indication of the hydration level and associated ventricular pre load status of the subject to determine the nature or extent of the intervention if required, wherein the intervention comprises a change in hydration level and/or use/change of any other therapeutic administered to influence the hydration and/or hemodynamic status of the subject (where the intervention may include modulating hydration level and/or modulating any other therapeutic administered to influence the hydration and/or hemodynamic status of the subject, and "modulating" may include initiating administration of a therapeutic or changing administration of a therapeutic) characterised in that the at least one stress related hemodynamic parameter is the respiratory variation in stroke volume or pressure and the at least one fluid responsiveness parameter is stroke volume variation or pulse pressure variation. These monitors and methods may incorporate any additional embodiment of the invention discussed herein, as appropriate.

The monitors of the invention are intended for use with multiple different patients (as opposed to being "single use" or fixed to one patient's requirements permanently). Thus, the monitors of the invention permit the set-up parameters and/or any calibration factors required for a particular patient to be entered on a case by case basis. In specific embodiments the monitor incorporates a suitable reader into which can be inserted a suitable data storage medium. The data storage medium is assigned to the patient in question and facilities use of the monitors for a range of patients with differing set-up requirements and/or calibration factors. This use of patient specific data storage media thus enhances the ease of use and speed of set-up of the monitors of the invention. Accordingly, the invention provides a single patient use data storage medium—in particular a computer readable medium—upon which may be stored individual patient data to permit hemodynamic monitoring of the patient. When read by the monitors of the invention, the data storage medium permits new patient data to be entered using the monitor and stored on the data storage medium. Alternatively, if patient data has been previously stored, reading of the data storage medium by the monitor permits recall of the patient data, thus preventing the requirement for the patient set-up and/or calibration to be repeated.

The data stored for each patient may comprise, consist essentially of or consist of details selected from Name, Height, Weight, Age and Body Surface Area. This data may be used by the monitors to produce a patient specific scaling factor. This may be nomogram based, as discussed herein, in certain embodiments. As would be immediately appreciated, the reader (computer) and data storage medium (computer readable medium) may take any suitable form such as CD or DVD-ROM, USB flash drive, radio frequency identification tag etc. In specific embodiments "smart cards" are employed. Any appropriate type of smart card (containing an integrated circuit chip) may be used, such as memory, CPU, contact, contactless and combi types. An individual data storage medium is assigned to an individual patient and allows repeat use for that patient. The previous set-up and/or calibration data is recalled when the medium is read by the monitor, thus facilitating ease and speed of patient monitoring—a particularly advantageous feature where critically ill patients are concerned. The data storage medium may have a predefined period of use. This is optionally printed on the medium itself. This allows control of the use of patient information. It also helps to prevent potentially misleading set-up and/or calibration information being employed for a patient a long time after the initial data was recorded (bearing in mind the primary application of the monitors of the invention). Thus, the patient data stored on the data storage medium may expire a period of hours, such as 5, 6, 7, 8, 9, 10 etc hours following first use.

The invention also relates to corresponding methods which utilise monitors of the invention in order to maintain or restore the hemodynamics of a subject. Accordingly, the invention provides a method of determining the requirement for, and/or if required the nature or extent of, and/or for monitoring the response to, an intervention by a carer for a subject in order to improve the hydration level and/or hemodynamic status of the subject during a period or periods of hemodynamic instability comprising:
(a) continuously analysing and processing at least a blood pressure or arterial volume/plethysmographic signal obtained from the subject using a processor comprising software arranged to derive a plurality of complementary parameters throughout the monitoring of the subject
(b) displaying images on a display means representing the derived plurality of complementary parameters, characterised in that the images comprise:
(1) at least one image representing graphically at least one stress related hemodynamic parameter plotted against time to provide an early/immediate indication of a change in the hemodynamic status and thus the requirement for an intervention
(2) at least one image representing graphically at least one fluid responsiveness parameter plotted against time to provide an indication of the hydration level and associated ventricular pre load status, wherein the intervention comprises a change in hydration level and/or use/change of any other therapeutic administered to influence the hydration and/or hemodynamic status of the subject (where the intervention may include modulating hydration level and/or modulating any other therapeutic administered to influence the hydration and/or hemodynamic status of the subject, and "modulating" may include initiating administration of a therapeutic or changing administration of a therapeutic).

The invention also provides a method of determining the requirement for, and/or if required the nature or extent of, and/or for monitoring the response to, an intervention by a carer for a subject in order to improve the hydration level and/or hemodynamic status of the subject during a period or periods of hemodynamic instability comprising:
(a) continuously analysing and processing at least a blood pressure or arterial volume/plethysmographic signal obtained from the subject using a processor comprising software arranged to derive a plurality of complementary parameters throughout the monitoring of the subject
(b) displaying images on a display means representing the derived plurality of complementary parameters, characterised in that the images comprise:
(1) at least one image representing graphically at least one stress related hemodynamic parameter plotted against time to provide an early/immediate indication of a change in the hemodynamic status and thus the requirement for an intervention
(2) at least one image representing graphically at least one fluid responsiveness parameter plotted against time to provide an indication of the hydration level and associated ventricular pre load status to determine the nature or extent of the intervention if required, wherein the intervention comprises a change in hydration level and/or use/change of any other therapeutic administered to influence the hydration and/or hemodynamic status of the subject (where the intervention may include modulating hydration level and/or modulating any other therapeutic administered to influence the hydration and/or hemodynamic status of the subject, and "modulating" may include initiating administration of a therapeutic or changing administration of a therapeutic)
characterised in that the at least one stress related hemodynamic parameter is the respiratory variation in stroke volume or pressure and the at least one fluid responsiveness parameter is stroke volume variation or pulse pressure variation.

The invention also provides a method of determining the requirement for, and/or if required the nature or extent of, and/or for monitoring the response to, an intervention by a carer for a subject in order to improve the hydration level and/or hemodynamic status of the subject during a period or periods of hemodynamic instability comprising:
(a) continuously analysing and processing at least a blood pressure or arterial volume/plethysmographic signal obtained from the subject using a processor comprising software arranged to derive a plurality of complementary parameters throughout the monitoring of the subject
(b) displaying images on a display means representing the derived plurality of complementary parameters, wherein the images comprise at least one image representing graphically the respiratory variation in at least one fluid responsiveness parameter plotted against time.

The methods of the invention may incorporate any and all relevant aspects and embodiments detailed in respect of the hemodynamic monitors of the invention. Accordingly, the description provided in respect of the monitors of the invention applies to the methods of the invention *mutatis mutandis* and is not repeated for reasons of conciseness.

The methods of the invention are generally non-invasive, since they begin at the step of processing the blood pressure or arterial volume/plethysmographic signal obtained from the subject. Thus, the monitors of the invention may be simply connected to existing patient monitors. However, in embodiments where the methods involve the step of obtaining the blood pressure or arterial volume/plethysmographic signal from the subject the methods may be invasive or non-invasive. This is determined primarily by how the blood pressure or arterial volume/plethysmographic signal obtained from the subject.

As discussed above, which discussion applies *mutatis mutandis*, the blood pressure or arterial volume/plethysmographic signal may be obtained from the subject through any suitable invasive or non-invasive means.

The methods of the invention may be utilised, in certain embodiments, to direct surgery and in particular surgical interventions. Where indications of the stability of the right heart/venous return/preload signal and/or the stability of the left ventricle signal are employed the methods of the invention may be utilised in order to determine the subject's response to a manual/mechanical intervention and guide the nature or extent of the manual/mechanical intervention accordingly. This may equally apply to the monitors of the invention described herein.

The invention will now be described with respect to the following non-limiting examples:

DETAILED DESCRIPTION OF THE INVENTION

Brief Description of the Figures

As shown in FIG. 1, the display means is a flat screen panel and incorporates an upper panel of images (1) displaying the following stress related hemodynamic parameters (y axis) plotted against time (x axis): —mean arterial pressure (MAP-mmHg) (2), heart rate (HR-bpm) (3), nominal stroke volume (nSV ml) (4) and nominal cardiac output (nCO-1/min) (5).

Figure 1:
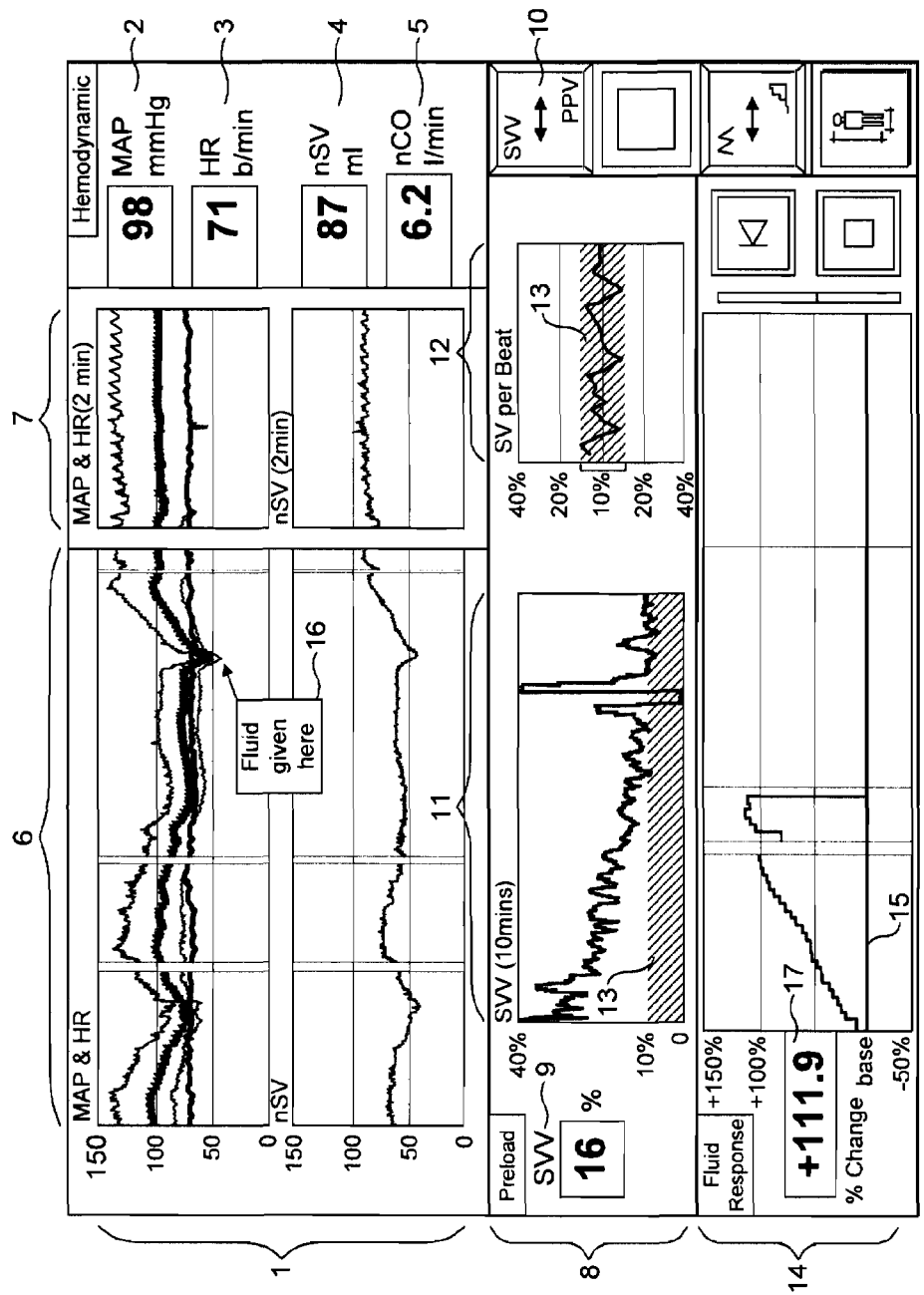
FIG. 1 is a representation of an exemplary display means of the invention.

Both trend displays (left hand panels (6)) and acute change displays, with an expanded y axis over a 2 minute time period, (right hand panels (7)) are utilised.

The display means incorporates a second panel (8) including the preload/fluid responsiveness parameter stroke volume variation (SVW-%) (9). This can be switched for pulse pressure variation as desired (PVV-%) (10). Both a trend display (11) and acute changes display (12) are utilised. The trend display shows SVV (%) plotted over time (10 minutes in this instance) and the acute changes (or signal quality) display shows SVV per beat, using an expanded y axis. Both the trend display and acute changes display incorporate a target zone (a shaded band in this case (13)) to provide an indication of the desired SVV value, namely around 10%.

The display means also incorporates a fluid/event response panel (14) presenting the percentage stroke volume response (15) following the intervention (16). The stroke volume response from the baseline is also shown as a numerical value (17). Other event response parameters may be selected as desired (9)

Figure 2:
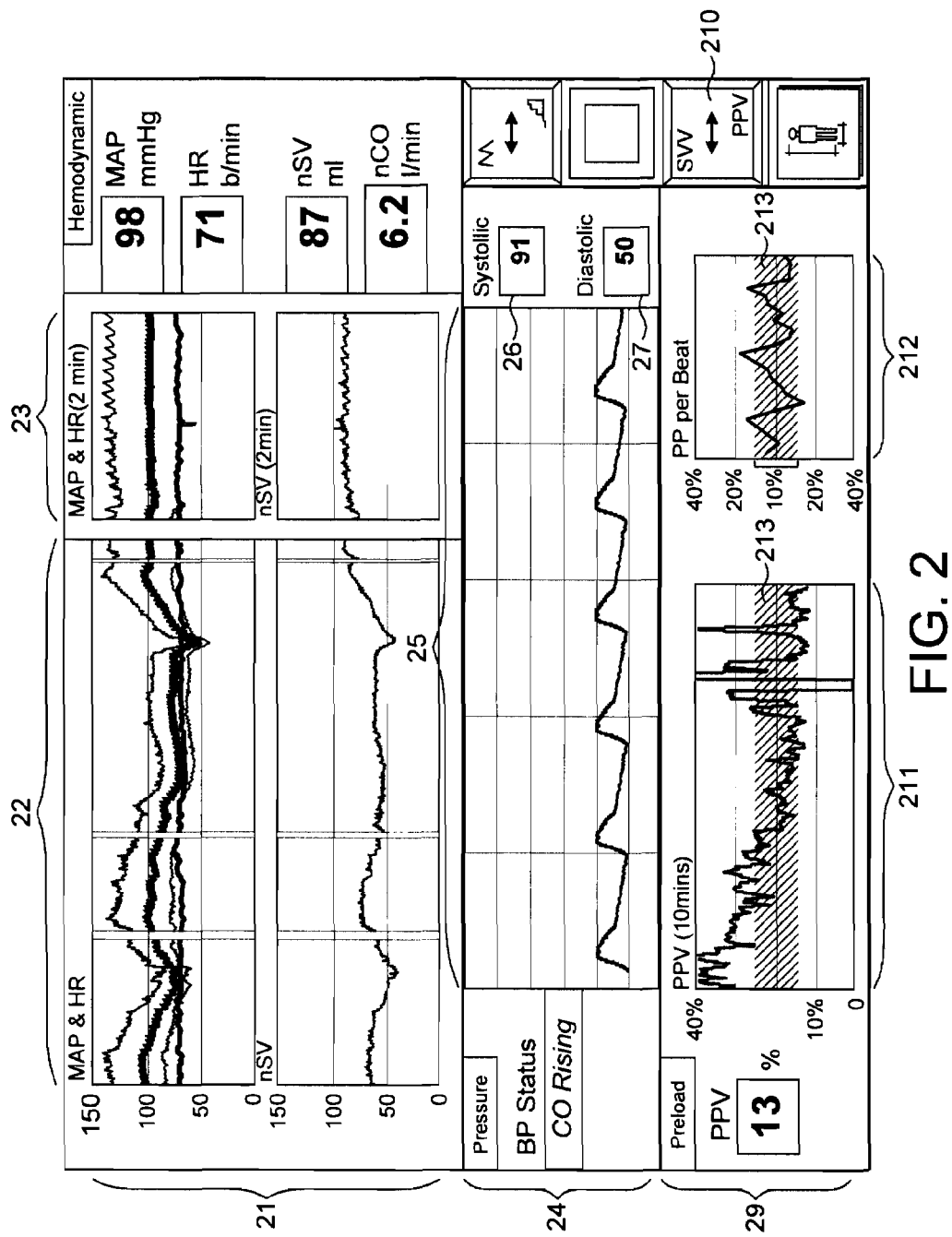
FIG. 2 is a representation of another display means of the invention, incorporating a display of raw analogue blood pressure data.

As shown in FIG. 2, the display means is a flat screen panel and incorporates an upper panel of images (21) identical to that shown in FIG. 1 and discussed above. Both trend displays (left hand panels (22)) and acute change displays, with an expanded y axis over a 2 minute time period, (right hand panels (23)) are utilised.

The display means incorporates a second panel (24) including an image of the raw analogue blood pressure signal (25). This signal is useful as an indication of the quality of the right heart signal. An indication of current systolic (26) and diastolic (27) blood pressure is also presented. Relevant outputs may also be displayed derived from this data, such as the change in cardiac output reflected in the signal (28). This display may be switched for an event response panel (14) in certain instances, such as the event response panel shown in FIG. 1.

The display means also incorporates a third panel including the preload/fluid responsiveness parameter pulse pressure variation (PVV-%) (29). This can be switched for stroke volume variation as desired (SVV-%) (210). Both a trend display (211) and acute changes display (212) are utilised. The trend display shows PVV (%) plotted over time (10 minutes in this instance) and the acute changes display shows PVV per beat, using an expanded y axis. Both the trend display and acute changes display incorporate a target zone (a shaded band in this case (213)) to provide an indication of the desired PVV value, namely around 10%-15%. The respiratory variation is a useful indicator of the signal quality of the right heart/venous return/preload status.

Hemodynamic parameters are derived from the patient's existing arterial pressure waveform using the PULSECO algorithm (software available from LIDCO Group Plc).

The basic set-up involves:
1. Connect the power cables to the monitor and an appropriate power socket.
2. Switch on the monitor via the power switch on the bottom.
3. Connect the appropriate blood pressure cable to the monitor of the invention and to the primary monitor.
4. Insert smartcard.
5. Note a new smartcard needs to be used when starting a new patient.
6. Orient the smartcard so that the logo can be read and the arrow points to the monitor.
7. Insert the card into the reader—the chip should be facing you.
8. When complete the Startup Screen will indicate 'Start New Patient'.
9. Press 'Start New Patient' to begin. The Setup Screen will be displayed next.
10. Enter the Patient's identification, age, height and weight.
11. Observe the blood pressure waveform matches the primary monitor.
12. Check the values for Systolic, Mean, Diastolic Blood Pressure and Heart Rate are within 5% of the primary monitor's display values.
14. Select the Main Screen button to begin monitoring.

Figure 3:
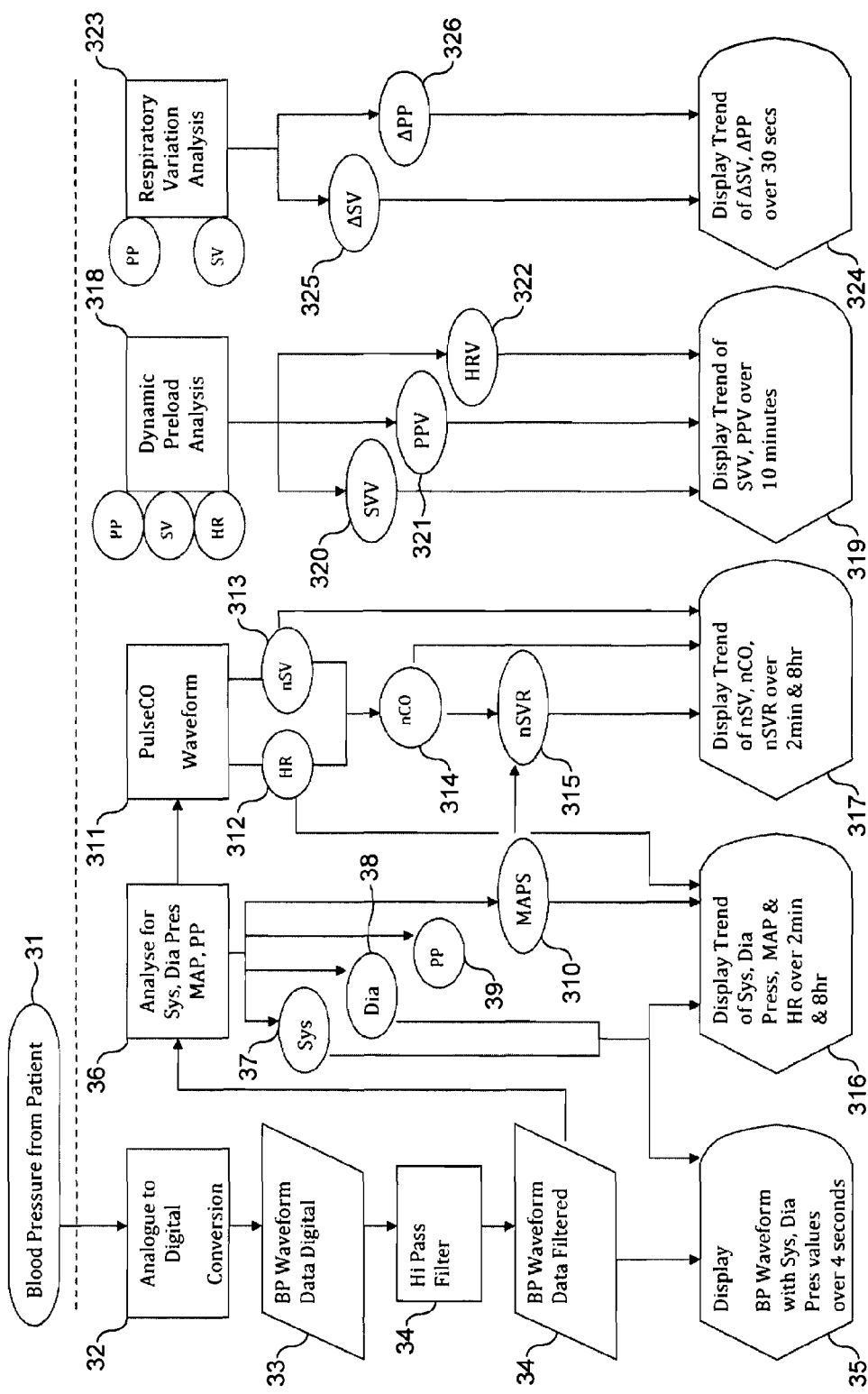
FIG. 3 is a flow chart showing the data handling and processing steps for generation of the display.

As shown in FIG. 3, an analogue blood pressure signal from the patient (31) is first converted to a digital signal (32) for example by a suitable transducer. The blood pressure waveform data (33) is then formulated and processed (34) to permit display of the blood pressure waveform (35). This waveform is analysed (36) to generate values for systolic pressure (37), diastolic pressure (38), pulse pressure (39) and mean arterial pressure (310). The PULSECO algorithm is applied to the waveform (311) and permits generation of heart rate (312), nominal stroke volume (313) and cardiac output (314) data. Nominal systemic vascular resistance (315) may also be calculated based upon cardiac output and mean arterial pressure values. These parameters can then be displayed as appropriate (316, 317). Generation of pulse pressure (39), stroke volume (313) and heart rate (312) data permit dynamic preload analysis to be carried out (318) generating displays (319) of one or more of stroke volume variation (320), pulse pressure variation (321) and heart rate variation (322). Pulse pressure (39) and stroke volume (313) data are also used in respiratory variation analysis (323) generating displays (324) of respiratory variations in stroke volume (325) and/or pulse pressure (326).

Figure 4:
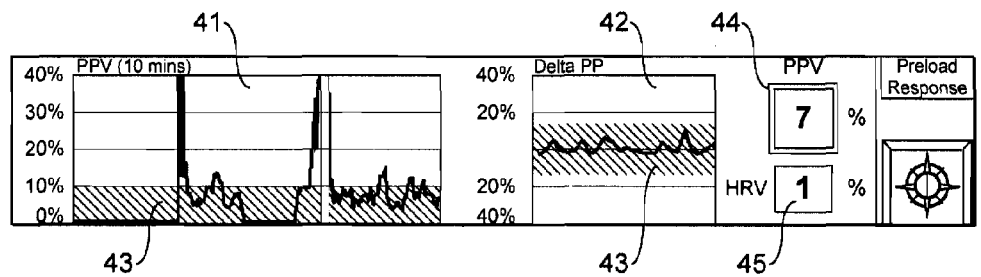
FIG. 4 shows an example of the fluid responsiveness display which forms an integral part of the monitors of the invention.

Turning now to FIG. 4, the fluid responsiveness display was developed to overcome problems identified by the inventors with previous monitors. The display is characterised by the following features:
1. A longer (10 mins) trend of the derived numeric value of the fluid responsiveness parameter, the numeric (41).
2. A short term (30 secs) trend of pulse pressure (PP) or stroke volume (SV) each heart beat displayed (line graph) as the percentage variation around a rolling mean value for the PP or SV (42). This shows the data in a much more physiologically relevant form.
3. Both trends incorporate a user definable target window (43) for the parameter.
4. The numerical value (updated every 4 secs) for SVV % or PPV % (44).
5. Heart Rate Variation may also be displayed numerically (45)

The long term trend (41) is designed to show how successful the physician has been in controlling the circulating blood volume of the patient and stopping the evolution of a hypovolemia (low effective circulating blood volume).

The short term trend (42) view is designed to, inter alia, display less processed individual "beat" data ie the SV and PP from a single beat and then show more visually (than is the case in the long term trend plot) the variation of these parameters across the respiratory cycle. This allows the user to assess the quality/relevance of the raw data. The short term line graph should show cyclical/sinusoidal variation with each ventilator cycle, against a mean reference value.

Figure 5:
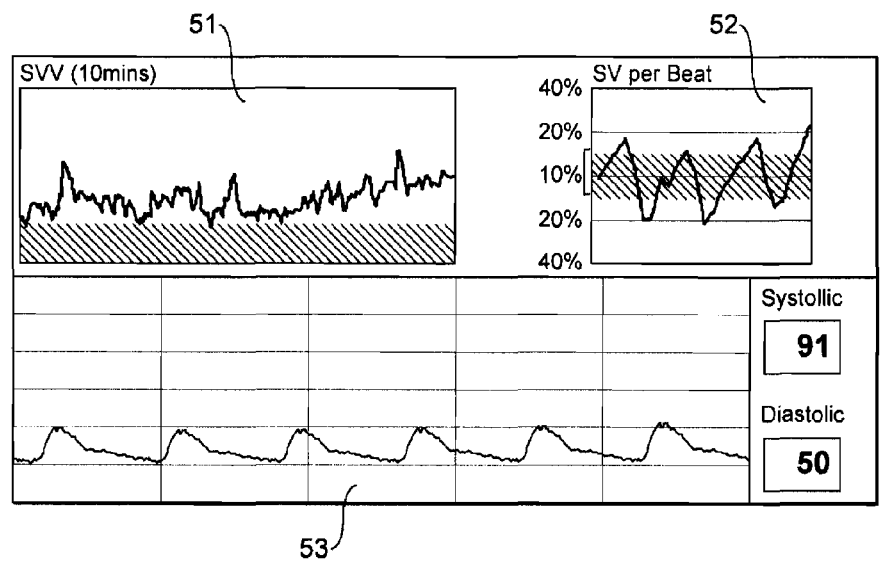
FIG. 5 shows an example of the fluid responses display incorporating a trend display of SVV and an acute changes display of respiratory variation in SV. Raw analogue blood pressure is also displayed as an additional signal quality indicator.

FIG. 5 presents one example of the application of the fluid responsiveness parameters display in terms of directing treatment. The long term trend display (51) shows the effects of blood loss over time ie a gradual evolution of hypovolemia (in particular, the data from the last 5 minutes). The short term trend (52) shows 2 full respiratory cycles. The user can see that the data is varying in a sinusoidal manner (as it should through the respiratory cycle). This observation, taken in combination with observing the blood pressure window below (53) and the heart rate variation number, means that the data presented is of good quality and can be interpreted as highly indicative of a progressive blood volume loss. This indicates to the anaesthetist that the long term trend towards hypovolemia is reliable and will need correction with the subsequent administration of fluids/blood.

Figure 6:
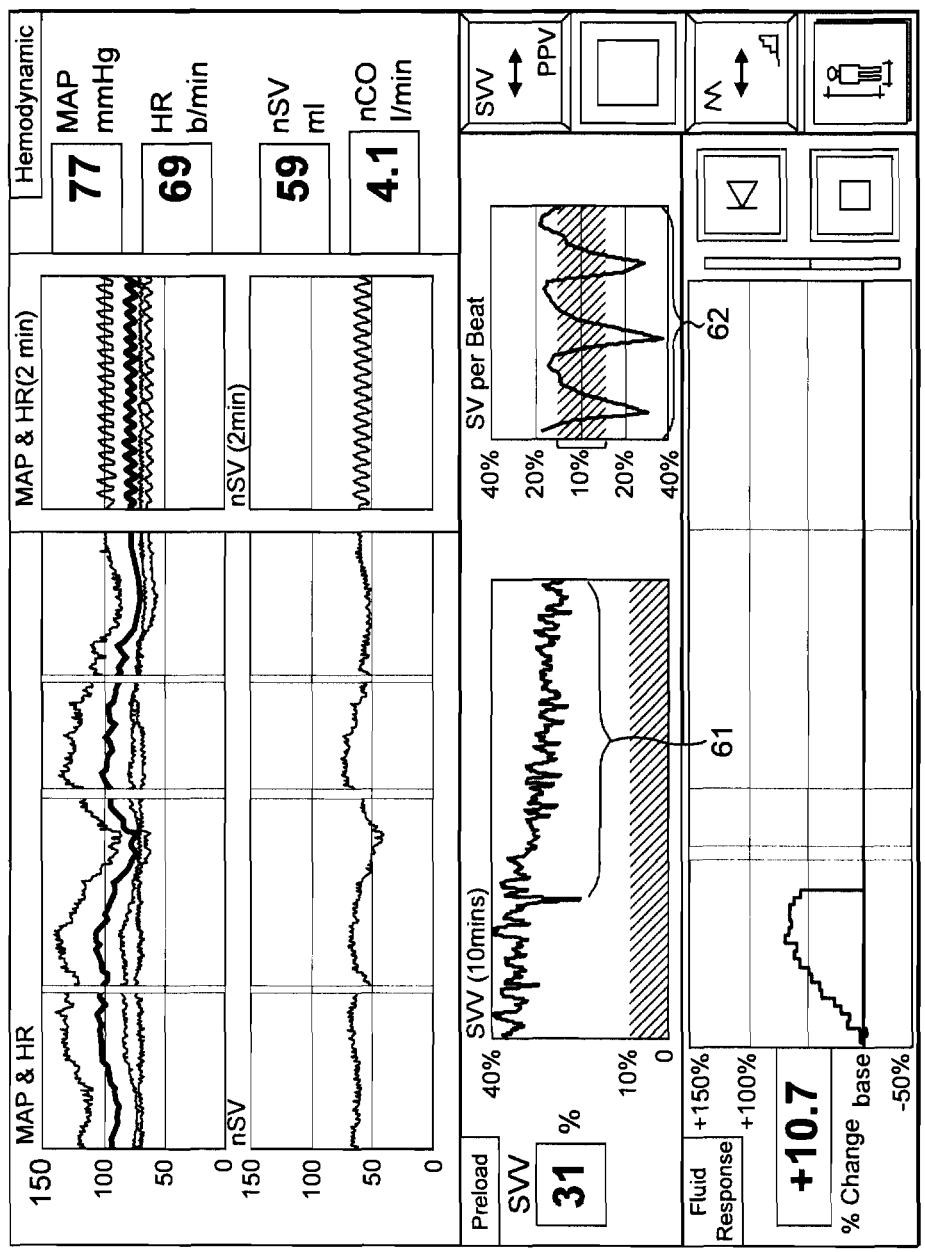
FIG. 6 is a further representation of the display means of the monitors of the invention.

As is shown in FIG. 6, the administration of fluid to a patient results in a downward trend in the SVV %. This is seen both in the long term trend window (61) and also in the decreasing amplitude (excursion in percentage from the mean) of variation across the respiratory cycle in the short term view (62). The response to the fluid administration is quicker and more intuitively obvious to see in the short term view—particularly if the long term view is of many hours in duration—when short term changes are not easily or quickly observable.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A hemodynamic monitor for a subject comprising:
    (a) a processor comprising software arranged to continuously analyze and process at least one of a blood pressure, arterial volume, or a plethysmographic signal obtained from the subject in order to derive a plurality of complementary parameters throughout the monitoring of the subject; and
    (b) a display,
    wherein the processor is configured to cause the display to display images representing the derived plurality of complementary parameters, wherein the images comprise:
        at least one image representing graphically at least one stress related hemodynamic parameter plotted against time to provide an early or immediate indication of a change in the hemodynamic status, thereby indicating a requirement for an intervention, wherein the at least one stress related hemodynamic parameter is selected from mean arterial pressure, systolic pressure, diastolic pressure, heart rate, stroke volume, cardiac output, systemic vascular resistance, and any of these parameters indexed to take account of the body surface area of the subject; and
        at least one image representing graphically at least one fluid responsiveness parameter plotted against time to provide an indication of hydration level and associated ventricular pre-load status of the subject, wherein the at least one fluid responsiveness parameter is selected from stroke volume variation (SVV), pulse pressure variation (PPV),
    wherein the controller is configured to derive the percentage variation around a rolling mean value for stroke volume (SV) or pulse pressure (PP) on a continuous beat-to-beat basis,
    wherein the processor is configured to cause the display to display the at least one image representing graphically at least one stress related hemodynamic parameter in the form of at least one image representing current changes in the stress related hemodynamic parameter plotted against time in combination with at least one image representing longer term changes in the stress related hemodynamic parameter plotted against time, wherein the at least one image displaying current changes in the stress related hemodynamic parameter comprises an expanded view of a portion of the image representing longer term changes in the stress related hemodynamic parameter, thus facilitating monitoring of current changes in the stress related hemodynamic parameter whilst simultaneously allowing monitoring of longer term changes in the stress related hemodynamic parameter, the at least one image displaying current changes in the stress related hemodynamic parameter and the at least one image representing longer term changes being simultaneously displayed in a spatially separate manner to ensure they can be viewed simultaneously without requiring input of a user, and
    wherein the processor is configured to cause the display to display:
    at least one image representing the percentage variation around the rolling mean value for stroke volume (SV) or pulse pressure (PP) plotted against time on a continuous beat-to-beat basis to indicate current changes in the at least one fluid responsiveness parameter, and
    the at least one image representing graphically the at least one fluid responsiveness parameter in the form of at least one image representing longer term changes in the fluid responsiveness parameter plotted against time, thus facilitating monitoring of current changes in the at least one fluid responsiveness parameter whilst simultaneously allowing monitoring of longer term changes in the at least one fluid responsiveness parameter, the at least one image representing the percentage variation and the at least one image representing longer term changes in the fluid responsiveness parameter being simultaneously displayed in a spatially separate manner to ensure they can be viewed simultaneously without requiring input of a user.

2. The hemodynamic monitor of claim 1, wherein the display interacts with the processor to display the images such that the images comprise at least one image representing graphically at least one response related parameter compared to the value of the parameter at a point of intervention to provide an indication of the desired or actual response of the subject to an intervention.

3. The hemodynamic monitor of claim 2 wherein the display interacts with the processor to plot the at least one response related parameter against time with reference to an indication of the value of the parameter at the point of intervention.

4. The hemodynamic monitor of claim 3 wherein the at least one response related parameter comprises stroke volume response to the intervention.

5. The hemodynamic monitor of claim 1 wherein the display interacts with the processor to plot respiratory variation in the at least one fluid responsiveness parameter per beat to provide an indication of stability of right heart, venous return, or pre-load signal.

6. The hemodynamic monitor of claim 1 wherein the display interacts with the processor to display at least one image representing the blood pressure signal obtained from the subject to provide an indication of stability of left ventricle signal.

7. A method of monitoring a subject during a period or periods of hemodynamic instability, the method comprising:
(a) continuously analysing and processing at least one of a blood pressure, arterial volume, or a plethysmographic signal obtained from the subject using a processor comprising software arranged to derive a plurality of complementary parameters throughout the monitoring of the subject; and
(b) displaying images on a display based on an interaction between the display and the processor, the images representing a derived plurality of complementary parameters, wherein the images comprise:
at least one image representing graphically at least one stress related hemodynamic parameter plotted against time to provide an early or immediate indication of a change in the hemodynamic status, thereby indicating a requirement for an intervention, wherein the at least one stress related hemodynamic parameter is selected from mean arterial pressure, systolic pressure, diastolic pressure, heart rate, stroke volume, cardiac output, systemic vascular resistance and any of these parameters indexed to take account of the body surface area of the subject; and
at least one image representing graphically at least one fluid responsiveness parameter plotted against time to provide an indication of the hydration level and associated ventricular pre-load status of the subject to determine whether an intervention is required, wherein the intervention comprises modulating hydration level or modulating other therapeutic administered to influence the hydration or hemodynamic status of the subject, wherein the at least one fluid responsiveness parameter is selected from stroke volume variation (SVV), pulse pressure variation (PPV), systolic pressure variation (SPV), and pulse oximetry plethysmographic waveform amplitude;
wherein the method comprises deriving the percentage variation around a rolling mean value for stroke volume (SV) or pulse pressure (PP) on a continuous beat-to-beat basis,
wherein the at least one image representing graphically at least one stress related hemodynamic parameter is displayed in the form of at least one image representing current changes in the stress related hemodynamic parameter plotted against time in combination with at least one image representing longer term changes in the stress related hemodynamic parameter plotted against time, wherein the at least one image displaying current changes in the stress related hemodynamic parameter comprises an expanded view of a portion of the image representing longer term changes in the stress related hemodynamic parameter thus facilitating monitoring of current changes in the stress related hemodynamic parameter whilst simultaneously allowing monitoring of longer term changes in the stress related hemodynamic parameter, the at least one image displaying current changes in the stress related hemodynamic parameter and the at least one image representing longer term changes being simultaneously displayed in a spatially separate manner to ensure they can be viewed simultaneously without requiring input of a user,
the method further comprises displaying at least one image representing the percentage variation around the rolling mean value for stroke volume (SV) or pulse pressure (PP) plotted against time on a continuous beat-to-beat basis to indicate current changes in the at least one fluid responsiveness parameter, and
wherein the at least one image representing graphically the at least one fluid responsiveness parameter is displayed in the form of at least one image representing longer term changes in the fluid responsiveness parameter plotted against time, thus facilitating monitoring of current changes in the at least one fluid responsiveness parameter whilst simultaneously allowing monitoring of longer term changes in the at least one fluid responsiveness parameter, the at least one image representing the percentage variation and the at least one image representing longer term changes in the fluid responsiveness parameter being simultaneously displayed in a spatially separate manner to ensure they can be viewed simultaneously without requiring input of a user.

8. The method of claim 7, wherein the display interacts with the processor to display the images so that they comprise at least one image representing graphically at least one response related parameter compared to the value of the parameter at a point of intervention to provide an indication of the desired or actual response of the subject to an intervention.

9. The method of claim 8, wherein the display interacts with the processor to plot at least one response related parameter against time with reference to an indication of the value of the parameter at the point of intervention.

10. The method of claim 9 wherein the at least one response related parameter comprises stroke volume response to the intervention.

11. The method of claim 7 wherein the display interacts with the processor to plot respiratory variation in the at least one fluid responsiveness parameter per beat to provide an early indication of stability of right heart, venous return, or pre-load signal.

12. The method of claim 7 wherein the display interacts with the processor to display at least one image representing the blood pressure signal obtained from the subject to provide an indication of stability of left ventricle signal.

13. The hemodynamic monitor of claim 1 wherein the display interacts with the processor to display the images so that the at least one image representing longer term changes in the parameter is auto-scaled to the duration of monitoring of the subject, or scaled to any representative longer period of time.

14. The method of claim 7 wherein the at least one image representing longer term changes in the parameter is auto-scaled to the duration of monitoring of the subject, or scaled to any representative longer period of time.

* * * * *